United States Patent
Penney

[11] 3,978,713
[45] Sept. 7, 1976

[54] LASER GENERATION OF ULTRASONIC WAVES FOR NONDESTRUCTIVE TESTING

[75] Inventor: Carl M. Penney, Scotia, N.Y.

[73] Assignee: General Electric Company, Schenectady, N.Y.

[22] Filed: May 27, 1975

[21] Appl. No.: 581,047

[52] U.S. Cl. ............................. 73/67.7; 73/71.5 US
[51] Int. Cl.² ..................................... G01N 29/04
[58] Field of Search .......... 73/67.5 R, 67.5 H, 67.6, 73/67.7, 67.8 R, 71.5 US

[56] References Cited
UNITED STATES PATENTS
3,782,177   1/1974   Hoop ............................ 73/67.5 R X OTHER PUBLICATIONS
"Excitation of Surface Elastic Waves by Transient Surface Heating" by Lee et al., from Applied Physics Letters 1/68 pp. 12–14.

"Generation of Elastic Waves by Transient Surface Heating" by White, from Journal of Applied Physics 12/63 pp. 3559–3567.

Primary Examiner—James J. Gill
Attorney, Agent, or Firm—Marvin Snyder; Joseph T. Cohen; Jerome C. Squillaro

[57] ABSTRACT

An object is tested for thickness or for presence and location of flaws by impacting a pulsed laser beam on the surface of the object so as to generate ultrasonic waves by rapid heating of a thin surface layer thereon. The reflected ultrasonic echo in the object is detected by monitoring surface motion with a rough surface interferometer.

8 Claims, 1 Drawing Figure

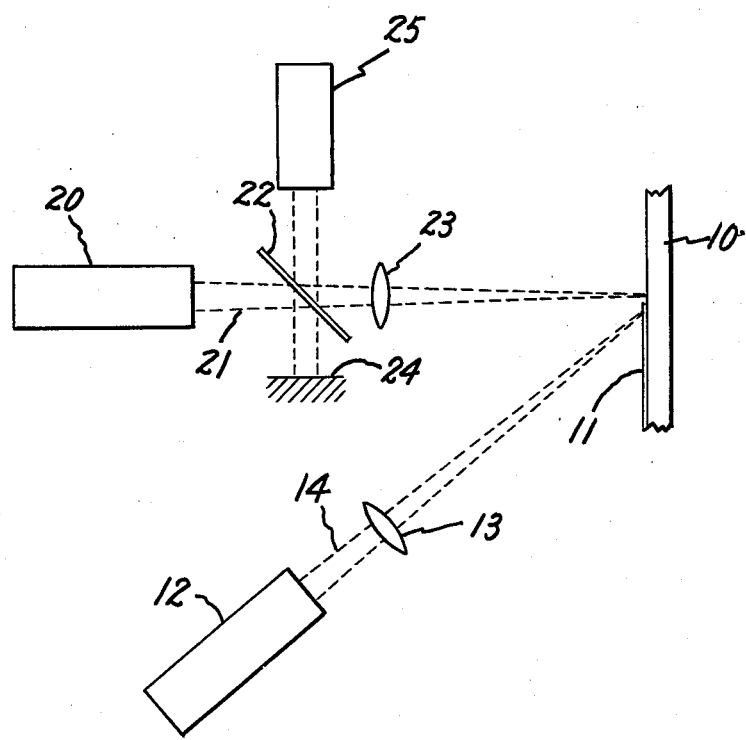

LASER GENERATION OF ULTRASONIC WAVES FOR NONDESTRUCTIVE TESTING

INTRODUCTION

This invention relates to generation of acoustic waves in a medium, and more particularly to a method and apparatus for generating and detecting ultrasonic waves in a medium without physically contacting such medium with a transducer.

Scattering of ultrasonic waves has been frequently utilized to locate boundaries and inhomogeneities in opaque media. It is often desirable to employ ultrasonic waves of the highest frequency (and thus the shortest wavelength) that can be transmitted into the material for a reasonable distance, in order to provide the best resolution. Resolution is approximately equal to one half the wavelength.

In order to locate boundaries and inhomogeneities in an opaque medium, it has been conventional to transmit high frequency ultrasonic waves into the medium and to receive the scattered signal in the medium by employment of a transducer coupled to the medium either mechanically or through a liquid bath. The inconvenience and inefficiency of this coupling are substantial drawbacks to conventional ultrasonic testing.

The invention described herein employs an optical noncontacting technique for introducing an ultrasonic signal into an object at a point on its surface, and detecting the reflected ultrasonic echo in the object. The signal is introduced into the object by impacting a pulsed laser beam on its surface. Ultrasonic waves are thereby generated in the object by rapid heating of a thin surface layer. The laser pulse intensity is selected to be below the threshold for deleterious surface damage to the object. Each ultrasonic wave may be in the form of a sudden shock, generated by a laser pulse with duration of about 10 nanoseconds. Alternatively, a train of waves concentrated into a narrow frequency band may be generated by a laser that is mode-locked or otherwise repetitively pulsed at a desired acoustic frequency; for example, a Q-switched, mode-locked neodymium glass laser can provide a train of 10 to 100 pulses, each about $10^{-11}$ seconds in duration, repeated at a frequency between 100 and 1000 MHz.

Motion of the surface may be monitored by a rough surface interferometer, which is capable of sensing a motion of $10^{-6}$ centimeters in 100 nanoseconds when monitoring a region of $10^{-2}$ centimeters diameter on an optically rough (or smooth) surface. While this sensitivity is several orders of magnitude lower than might be expected from an ultrasonic transducer, power coupled into the acoustic wave by the pulsed laser can be several orders of magnitude greater than furnished by the transducer, thus offsetting any possible loss of sensitivity due to omitting the ultrasonic transducer in making measurements.

Accordingly, one object of the invention is to provide a method and apparatus for generating intense, high frequency acoustic waves in solid and liquid media.

Another object is to provide a method and apparatus for nondestructively determining physical characteristics of a medium without requiring that the medium be physically contacted by a transducer.

Another object is to provide an optical, high speed, noncontacting acoustic probe which employs ultrasonic pulses.

Briefly, in accordance with a preferred embodiment of the invention, a method of generating high frequency acoustic waves in a solid object comprises selecting regions to undergo intense optical radiation on an object to be examined, and irradiating the selected regions with intense pulses of optical energy at an irradiation density below the threshold for deleterious surface damage to such object.

In accordance with another preferred embodiment of the invention, apparatus for nondestructively testing a solid medium comprises means for directing an intense pulse of optical energy onto the medium, and optical means responsive to surface movement of the medium for detecting an acoustic pulse echo in the medium.

BRIEF DESCRIPTION OF THE DRAWING

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which the single FIGURE is a schematic illustration of an arrangement for performing acoustical testing on a medium in accordance with the invention.

DESCRIPTION OF TYPICAL EMBODIMENTS

In the FIGURE, a test piece 10 is illustrated receiving pulses, typically in the near-ultraviolet waveband (e.g., 337.1 nanometers) from a relatively low power pulsed laser 12, such as a nitrogen laser. Test piece 10, typically metallic, may be coated with a flat, black paint 11 in the region illuminated by laser 12, if desired, to increase optical absorption. Light beam 14 from laser 12, focused through a lens system 13, irradiates the test piece, with pulses. For a test piece comprised of aluminum, the pulses are typically of one millijoule in energy and 10 nanoseconds duration. In this fashion, acoustic pulses are generated in the test piece surface and propagate through the material.

It is believed that the acoustic wave generated in the test piece is the result of a sudden expansion of the metal surface caused by absorption of the optical energy. Yet the relatively low power density (approximately $10^9$ watts/meter$^2$) of such laser is several orders of magnitude below that at which deleterious damage to the test piece surface occurs (i.e., $10^{11}$ watts/meter$^2$ for polished aluminum). Such damage would occur if the temperature of a thin surface layer were to approach its vaporization temprature. However, a coarse surface layer can withstand greater damage than a finely-finished surface layer before the damage becomes deleterious or beyond simple repair.

Despite the relatively low power density of laser 12, the high frequency acoustic waves generated in the test piece as a result of the laser irradiation are of intensity beyond the generating capability of a conventional transducer. These waves can be detected by a conventional detector at a much greater working distance through the probed material, thereby enhancing flaw detection.

Measurement of acoustic pulses in the test piece may conveniently be made with a rough surface interferometer arrangement including a conventional CW laser 20 having the portion of its light beam 21 which passes through a beam splitter 22 focused by a lens system 23 onto the surface of test piece 10. The portion of incident light beam 21 reflected by beam splitter 22 is reflected by a mirror 24 back through beam splitter 22 onto a light detector 25.

Motion of the surface of test piece 10 is sensed by light detector 25 as a result of optical interference between coherent radiation from CW laser 20 reflected by mirror 24 and reflected by test piece 10. Detecting parameters of the resulting optical interference provides an indication of test piece thickness and location of flaws in the test piece. The interferometer has capability of sensing a motion of $10^{-6}$ centimeters in $10^{-8}$ seconds when monitoring a region of $10^{-2}$ centimeters diameter on an optically rough (or smooth) surface.

By employing a repetitively pulsed laser (such as a mode-locked laser) to impact coherent optical energy upon the test piece, the resulting coherent ultrasonic wave in the test piece can, if desired, be monitored by holographic techniques, particularly stroboscopic holography. This permits visualization of the complete, scattered optical wave pattern emanating from the test piece, allowing flaws to be located in three dimensions.

The foregoing describes a method and apparatus for nondestructively determining physical characteristics of a nondestructively determining solid or liquid medium without requiring that it be physically contacted by a transducer. Intense, high frequency acoustic waves are also generated in the medium without making any physical contact therewith. The method and apparatus provides an all-optical, high speed, noncontacting acoustic probe which propagates ultrasonic pulses through the medium and detects scattered acoustic waves to determine physical characteristics of the medium and to locate flaws therein.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

I claim:

1. In apparatus for nondestructively testing a medium by generating pulses of ultrasonic energy within said medium and measuring the response of said medium to said pulses, the improvement wherein at least a portion of said medium comprises a surface absorbent to optical energy and having a characteristic damage threshold for deleterious surface damage, and further including means for directing an intense pulse of optical energy below said damage threshold onto the absorbent portion of said medium to generate said pulses of ultrasonic energy within said medium.

2. The apparatus of claim 1 wherein said means for directing an intense pulse of optical energy onto said medium comprises a pulsed laser.

3. The apparatus of claim 2 wherein said pulsed laser is repetitively pulsed at a desired acoustic frequency to concentrate the generated pulses of ultrasonic energy in a narrow frequency band.

4. Apparatus for nondestructively testing a solid medium, comprising:
   means for directing an intense pulse of coherent optical energy onto said medium to generate acoustic waves therein; and
   optical means responsive to movement of the surface of said medium for detecting an acoustic pulse echo in the medium.

5. The apparatus of claim 4 wherein said coherent optical energy is in the near-ultraviolet range.

6. The apparatus of claim 4 wherein said means for directing an intense pulse of coherent optical energy onto said medium comprises a pulsed laser.

7. The apparatus of claim 6 wherein said pulsed laser is repetitively pulsed at a desired acoustic frequency to concentrate the generated acoustic waves in a narrow frequency band.

8. The apparatus of claim 4 wherein said optical means responsive to movement of the surface of said medium comprises rough surface interferometer means.

* * * * *